(12) United States Patent
Robinson et al.

(10) Patent No.: US 11,544,845 B2
(45) Date of Patent: Jan. 3, 2023

(54) DIGITAL IMAGING SYSTEMS AND METHODS OF ANALYZING PIXEL DATA OF AN IMAGE OF A USER'S BODY BEFORE REMOVING HAIR FOR DETERMINING A USER-SPECIFIC TRAPPED HAIR VALUE

(71) Applicant: THE GILLETTE COMPANY LLC, Boston, MA (US)

(72) Inventors: Susan Clare Robinson, Windsor (GB); Leigh Knight, Reading (GB); Tina Susannah Clarelli, Bramley (GB)

(73) Assignee: The Gillette Company LLC, Boston, MA (US)

( * ) Notice: Subject to any disclaimer, the term of this patent is extended or adjusted under 35 U.S.C. 154(b) by 75 days.

(21) Appl. No.: 16/919,294

(22) Filed: Jul. 2, 2020

(65) Prior Publication Data
US 2022/0005186 A1    Jan. 6, 2022

(51) Int. Cl.
*G06T 7/00* (2017.01)
*G06T 11/60* (2006.01)
(Continued)

(52) U.S. Cl.
CPC ............ *G06T 7/0012* (2013.01); *A45D 44/00* (2013.01); *G06N 5/04* (2013.01); *G06N 20/00* (2019.01);
(Continued)

(58) Field of Classification Search
CPC ................. G06T 7/0012; G06T 11/60; G06T 2207/20081; G06T 2207/30196;
(Continued)

(56) References Cited

U.S. PATENT DOCUMENTS 5,252,331 A * 10/1993 Curtis ...................... A61K 8/31
424/401
9,013,567 B2    4/2015 Clemann et al.
(Continued)

FOREIGN PATENT DOCUMENTS

EP         3651949 A1    5/2020
WO    WO-2011106792 A2    9/2011
WO    WO-2019136354 A1    7/2019

OTHER PUBLICATIONS

ScienceInsider: Youtube video "What Are Ingrown Hairs—And How To Treat Them", Published Jun. 2, 2018. https://www.youtube.com/watch?v=laevAwpnPjc (Year: 2018).*

*Primary Examiner* — Sing-Wai Wu
(74) *Attorney, Agent, or Firm* — Kevin C. Johnson

(57) ABSTRACT

A digital imaging method of analyzing pixel data of an image of a user's body for determining a user-specific trapped hair value before removing hair is disclosed. The digital imaging method includes: aggregating training images of respective individuals' bodies before removing hair; training, using the pixel data of the training images, a trapped hair model to determine trapped hair values associated with a trapped hair scale ranging from least trapped hair to most trapped hair; receiving an image of a user's body before removing hair; analyzing the user image using the trapped hair model to determine a user-specific trapped hair value; generating a user-specific electronic recommendation designed to address a feature identifiable within the pixel data of the user's body based on the user-specific trapped hair value; and rendering the recommendation on a display screen of a user computing device.

23 Claims, 4 Drawing Sheets

(51) Int. Cl.

| | |
|---|---|
| *G06N 20/00* | (2019.01) |
| *G06V 10/764* | (2022.01) |
| *G06V 40/10* | (2022.01) |
| *A45D 44/00* | (2006.01) |
| *G06N 5/04* | (2006.01) |
| *G06Q 10/06* | (2012.01) |
| *G06Q 30/06* | (2012.01) |
| *G16H 50/50* | (2018.01) |
| *G16H 50/30* | (2018.01) |
| *G16H 50/20* | (2018.01) |
| *G06Q 20/18* | (2012.01) |

(52) U.S. Cl.
CPC ... *G06Q 10/06316* (2013.01); *G06Q 30/0631* (2013.01); *G06Q 30/0643* (2013.01); *G06T 11/60* (2013.01); *A45D 2044/007* (2013.01); *G06Q 20/18* (2013.01); *G06T 2207/20081* (2013.01); *G06T 2207/30196* (2013.01); *G16H 50/20* (2018.01); *G16H 50/30* (2018.01); *G16H 50/50* (2018.01)

(58) Field of Classification Search
CPC .......... G06Q 30/0631; G06Q 30/0643; G06Q 20/18; A45D 2044/007; G16H 50/20; G16H 50/30; G16H 50/50
See application file for complete search history.

(56) References Cited

U.S. PATENT DOCUMENTS

| | | | |
|---|---|---|---|
| 2009/0024023 A1* | 1/2009 | Welches | A61B 90/37 |
| | | | 600/424 |
| 2011/0016001 A1 | 1/2011 | Schieffelin | |
| 2013/0231618 A1* | 9/2013 | Zupkosky | B26B 21/4081 |
| | | | 604/290 |
| 2017/0330264 A1 | 11/2017 | Youssef et al. | |
| 2018/0040053 A1* | 2/2018 | Robinson | G06Q 30/0621 |
| 2018/0247365 A1 | 8/2018 | Cook et al. | |
| 2019/0166980 A1 | 6/2019 | Huang et al. | |
| 2019/0355115 A1 | 11/2019 | Niebauer et al. | |
| 2020/0294234 A1* | 9/2020 | Rance | A61B 5/7267 |

* cited by examiner

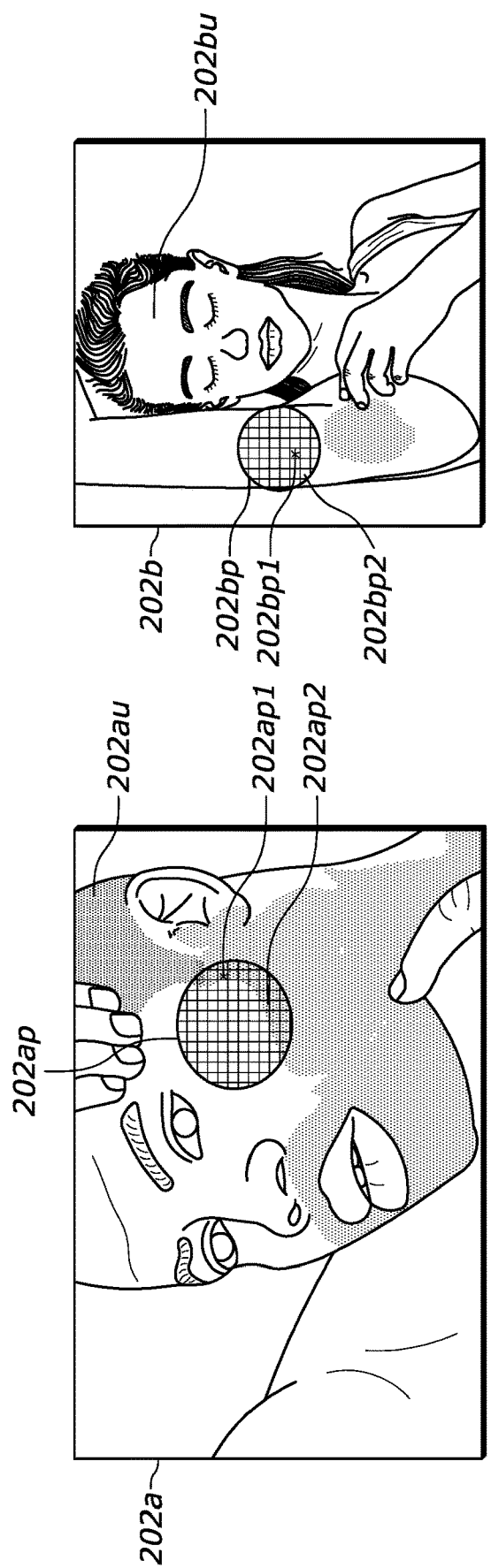
FIG. 2A
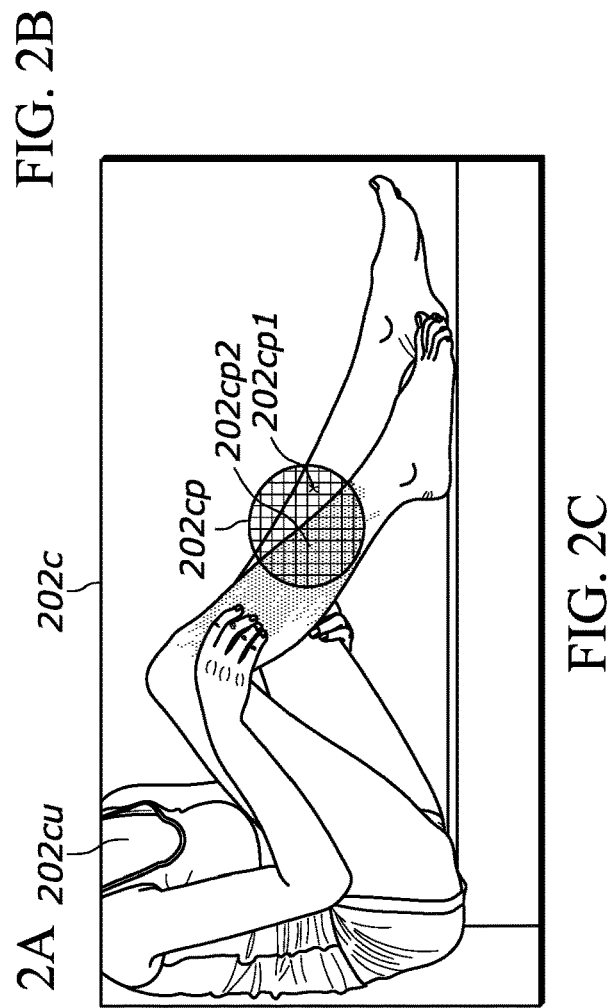
FIG. 2B
FIG. 2C

DIGITAL IMAGING SYSTEMS AND METHODS OF ANALYZING PIXEL DATA OF AN IMAGE OF A USER'S BODY BEFORE REMOVING HAIR FOR DETERMINING A USER-SPECIFIC TRAPPED HAIR VALUE

FIELD

The present disclosure generally relates to digital imaging systems and methods, and more particularly to, digital imaging systems and methods for analyzing pixel data of an image of a user's body before removing hair for determining a user-specific trapped hair value.

BACKGROUND

Generally, individuals today who wish to remove hair from various areas of their bodies have the option of using many different hair removal methods, including shaving using a wet razor, shaving using a dry shaver, epilators, waxes, and other methods. In some instances, the use of each of these methods of hair removal can cause hair to become trapped or ingrown. Variations in individuals' expertise levels with different hair removal methods, sensitivity levels and skin types, as well as variations in areas of the body where each individual is removing hair and variations in users' individual techniques as they use these hair removal methods lead to varying rates or severity of these trapped or ingrown hairs for each of these methods between individuals. That is, one user may often develop trapped or ingrown hairs before using a wet razor to remove hair, while another user using the same wet razor may remove hair with fewer (or no) trapped or ingrown hair. Trapped and ingrown hair can be painful and irritating for users, can be cosmetically embarrassing, and, importantly, can cause an amplification of skin problems such as irritation and damage when the user next comes to remove hair.

Thus, a problem arises for existing hair removal methods, and the use thereof, where individuals knowingly or unknowingly utilize hair removal methods that cause high rates or severity of trapped or ingrown hair for their specific sensitivity level, skin type, etc., while other hair removal methods are better suited for their specific needs and cause lower rates or severity of trapped or ingrown hair for their specific sensitivity level, skin type, etc. As one example, pseudofolliculitis barbae (PFB) is an extreme form of trapped hairs that particularly affects the skin of Black individuals, generally due to the curved nature of the hair follicle, and can be a challenge for affected individuals when using certain hair removal methods, such as shaving. The problem is acutely pronounced given the various versions, brands, and types of hair removal methods currently available to individuals, where each of these different versions, brands, and types of hair removal methods have different ingredients, components, blades, sharpness, and/or otherwise different configurations, all of which can affect rates or severity of trapped or ingrown hair for users having varying sensitivity levels, skin types, and techniques, as well as for expertise levels in using the products and varying areas of the body where each individual is removing hair. These problems are particularly acute because such existing hair removal methods provide little or no feedback or guidance to assist the individual in determining which methods of hair removal increase or decrease rates or severity of trapped or ingrown hair for a particular user, or in comparing rates or severity of trapped or ingrown hair between methods.

For the foregoing reasons, there is a need for digital imaging systems and methods for analyzing pixel data of an image of a user's body before removing hair for determining a user-specific trapped hair value.

SUMMARY

Generally, as described herein, the digital imaging systems and methods for analyzing pixel data of an image of a user's body before removing hair for determining a user-specific trapped hair value provide a digital imaging and artificial intelligence (AI) based solution for overcoming problems that arise from trapped or ingrown hairs resulting from hair removal methods. The digital systems and methods allow a user to submit a specific user image to imaging server(s) (e.g., including its one or more processors), or otherwise a computing device (e.g., such as locally on the user's mobile device), where the imaging server(s) or user computing device implements or executes a trapped hair model trained with pixel data of potentially 10,000s (or more) images of individuals before removing hair. The trapped hair model may generate, based on a determined user-specific trapped hair value, a user-specific electronic recommendation designed to address at least one feature identifiable within the pixel data comprising at least a portion of the user's body or body area before removing hair. For example, the at least one feature can comprise pixels or pixel data indicative of a number of trapped or ingrown hairs, a severity of any trapped or ingrown hair, etc. In some embodiments, the user-specific recommendation (and/or product specific recommendation) may be transmitted via a computer network to a user computing device of the user for rendering on a display screen. In other embodiments, no transmission to the imaging server of the user's specific image occurs, where the user-specific recommendation (and/or product specific recommendation) may instead be generated by the trapped hair model, executing and/or implemented locally on the user's mobile device and rendered, by a processor of the mobile device, on a display screen of the mobile device. In various embodiments, such rendering may include graphical representations, overlays, annotations, and the like for addressing the feature in the pixel data.

More specifically, as described herein, a digital imaging method of analyzing pixel data of at least one image of a user's body for determining a user-specific trapped hair value before removing hair is disclosed, the digital imaging method comprising the steps of: aggregating, at one or more processors communicatively coupled to one or more memories, a plurality of training images of a plurality of individuals before removing hair, each of the training images comprising pixel data of a respective individual's body or body area before removing hair; training, by the one or more processors, with the pixel data of the plurality of training images, a trapped hair model operable to determine trapped hair values associated with a trapped hair scale ranging from least trapped hair to most trapped hair; receiving, at the one or more processors, at least one image of a user, the at least one image captured by a digital camera, and the at least one image comprising pixel data of the user's body or body area before removing hair; analyzing by the trapped hair model executing on the one or more processors, the at least one image captured by the digital camera to determine a user-specific trapped hair value; generating, by the one or more processors, based on the user-specific trapped hair value, at least one user-specific electronic recommendation designed to address at least one feature identifiable within the pixel data of the user's body or body area; and rendering, on a display screen of a user computing device, the at least one user-specific electronic recommendation.

In addition, as described herein, a digital imaging system is disclosed, configured to analyze pixel data of at least one image of a user's body for determining a user-specific trapped hair value before removing hair, the digital imaging system comprising: an imaging server comprising a server processor and a server memory; an imaging application (app) configured to execute on a user computing device comprising a device processor and a device memory, the imaging app communicatively coupled to the imaging server; and a trapped hair model trained with pixel data of a plurality of training images of individuals and operable to determine trapped hair values associated with a trapped hair scale ranging from least trapped hair to most trapped hair, wherein the trapped hair model is configured to execute on the server processor or the device processor to cause the server processor or the device processor to: receive at least one image of a user, the at least one image captured by a digital camera, and the at least one image comprising pixel data of the user's body or body area before removing hair, analyze, by the trapped hair model, the at least one image captured by the digital camera to determine a user-specific trapped hair value, generate, based on the user-specific trapped hair value, at least one user-specific electronic recommendation designed to address at least one feature identifiable within the pixel data comprising the user's body or body area before removing hair, and render, on a display screen of the user computing device of the user, the at least one user-specific electronic recommendation.

Further, as described herein, A tangible, non-transitory computer-readable medium is disclosed, storing instructions for analyzing pixel data of at least one image of a user's body for determining a user-specific trapped hair value before removing hair, that when executed by one or more processors cause the one or more processors to: aggregate, at one or more processors communicatively coupled to one or more memories, a plurality of training images of a plurality of individuals, each of the training images comprising pixel data of a respective individual before removing hair; train, by the one or more processors with the pixel data of the plurality of training images, a trapped hair model operable to determine trapped hair values associated with a trapped hair scale ranging from least trapped hair to most trapped hair; receive, at the one or more processors, at least one image of a user, the at least one image captured by a digital camera, and the at least one image comprising pixel data of the user's body or body area before removing hair; analyze, by the trapped hair model executing on the one or more processors, the at least one image captured by the digital camera to determine a user-specific trapped hair value; generate, by the one or more processors based on the user-specific trapped hair value, at least one user-specific electronic recommendation designed to address at least one feature identifiable within the pixel data comprising the user's body or body area before removing hair; and render, on a display screen of a user computing device, the at least one user-specific electronic recommendation.

In accordance with the above, and with the disclosure herein, the present disclosure includes improvements in computer functionality or in improvements to other technologies at least because the disclosure describes that, e.g., an imaging server, or otherwise computing device (e.g., a user computer device), is improved where the intelligence or predictive ability of the imaging server or computing device is enhanced by a trained (e.g., machine learning trained) trapped hair model. The trapped hair model, executing on the imaging server or computing device, is able to accurately identify, based on pixel data of other individuals, a user-specific trapped hair value and a user-specific electronic recommendation designed to address at least one feature identifiable within the pixel data of a specific user's body or body area before removing hair. That is, the present disclosure describes improvements in the functioning of the computer itself or "any other technology or technical field" because an imaging server or user computing device, is enhanced with a plurality of training images (e.g., 10,000s of training images and related pixel data as feature data) to accurately predict, detect, or determine pixel data of a user-specific images, such as newly provided customer images. This improves over the prior art at least because existing systems lack such predictive or classification functionality and are simply not capable of accurately analyzing user-specific images to output a predictive result to address at least one feature identifiable within the pixel data comprising the at least one image of the user's body or body area before removing hair.

For similar reasons, the present disclosure relates to improvement to other technologies or technical fields at least because the present disclosure describes or introduces improvements to computing devices in the field of hair removal, whereby the trained trapped hair model executing on the imaging devices or computing devices improve the field of hair removal with digital and/or artificial intelligence based analysis of user or individual images to output a predictive result to address at least one feature identifiable within the user-specific pixel data of the user's body or body area before removing hair.

In addition, the present disclosure includes specific features other than what is well-understood, routine, conventional activity in the field, or adding unconventional steps that confine the claim to a particular useful application, e.g., analyzing pixel data of an image of a user's body before removing hair for determining a trapped hair value, as described herein.

Advantages will become more apparent to those of ordinary skill in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein:

FIG. 2A illustrates an example image and its related pixel data that may be used for training and/or implementing a trapped hair model, in accordance with various embodiments disclosed herein.

FIG. 2B illustrates a further example image and its related pixel data that may be used for training and/or implementing a trapped hair model, in accordance with various embodiments disclosed herein.

FIG. 2C illustrates a further example image and its related pixel data that may be used for training and/or implementing a trapped hair model, in accordance with various embodiments disclosed herein.

The Figures depict preferred embodiments for purposes of illustration only. Alternative embodiments of the systems and methods illustrated herein may be employed without departing from the principles of the invention described herein.

DETAILED DESCRIPTION OF THE INVENTION

Figure 1:
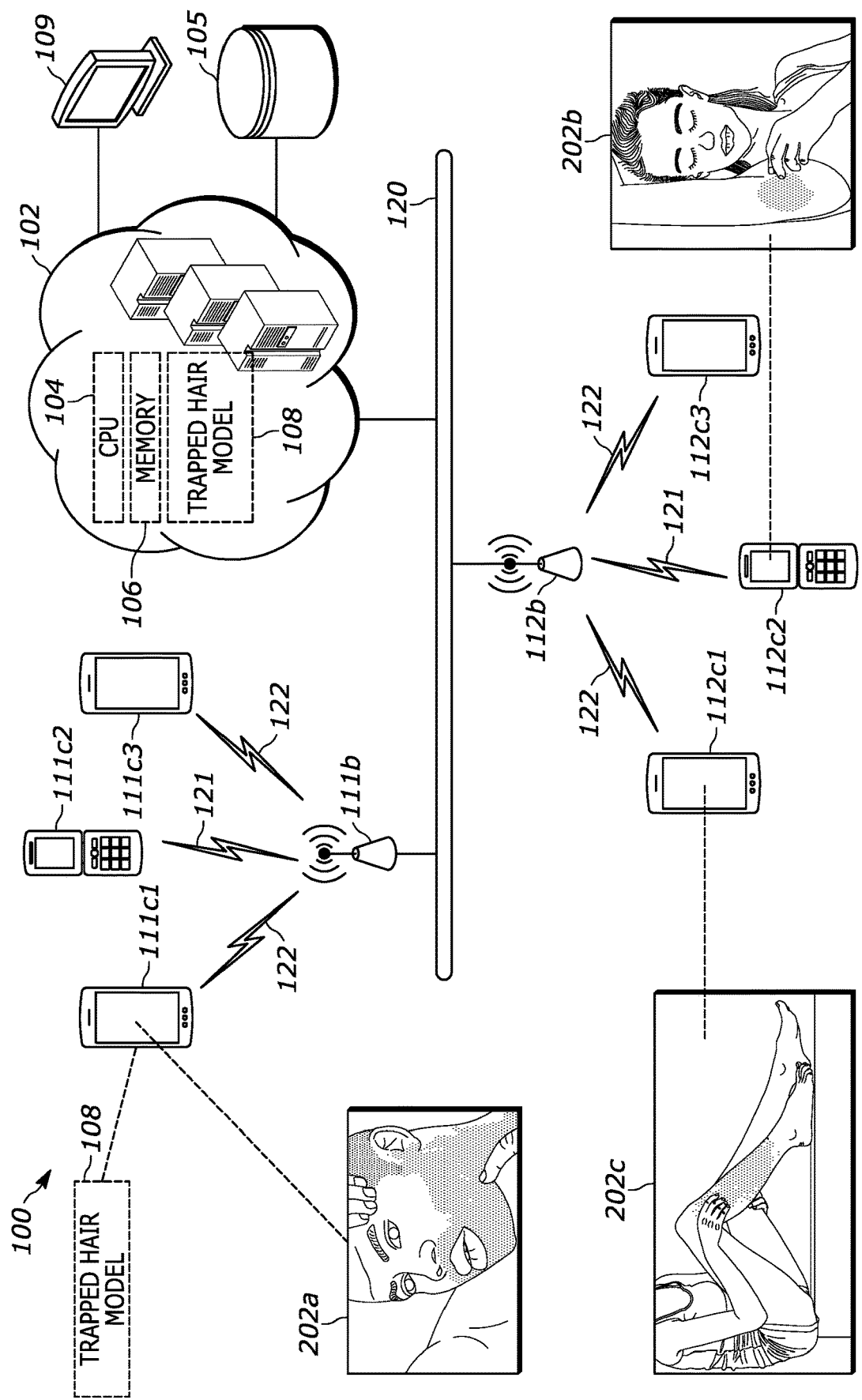
FIG. 1 illustrates an example digital imaging system configured to analyze pixel data of an image of a user's body before removing hair for determining a trapped hair value, in accordance with various embodiments disclosed herein.

FIG. 1 illustrates an example digital imaging system 100 configured to analyze pixel data of an image (e.g., any one or more of images 202*a*, 202*b*, and/or 202*c*) of a user's body before removing hair for determining a trapped hair value, in accordance with various embodiments disclosed herein. As referred to herein, a "body" may refer to any portion of the human body including the torso, waist, face, head, arm, leg, or other appendage or portion or part of the body thereof. In the example embodiment of FIG. 1, digital imaging system 100 includes server(s) 102, which may comprise one or more computer servers. In various embodiments server(s) 102 comprise multiple servers, which may comprise a multiple, redundant, or replicated servers as part of a server farm. In still further embodiments, server(s) 102 may be implemented as cloud-based servers, such as a cloud-based computing platform. For example, server(s) 102 may be any one or more cloud-based platform(s) such as MICROSOFT AZURE, AMAZON AWS, or the like. Server(s) 102 may include one or more processor(s) 104 as well as one or more computer memories 106. Server(s) 102 may be referred to herein as "imaging server(s)."

The memories 106 may include one or more forms of volatile and/or non-volatile, fixed and/or removable memory, such as read-only memory (ROM), electronic programmable read-only memory (EPROM), random access memory (RAM), erasable electronic programmable read-only memory (EEPROM), and/or other hard drives, flash memory, MicroSD cards, and others. The memorie(s) 106 may store an operating system (OS) (e.g., Microsoft Windows, Linux, Unix, etc.) capable of facilitating the functionalities, apps, methods, or other software as discussed herein. The memorie(s) 106 may also store a trapped hair model 108, which may be an artificial intelligence based model, such as a machine learning model trained on various images (e.g., images 202*a*, 202*b*, and/or 202*c*), as described herein. Additionally, or alternatively, the trapped hair model 108 may also be stored in database 105, which is accessible or otherwise communicatively coupled to imaging server(s) 102. The memories 106 may also store machine readable instructions, including any of one or more application(s), one or more software component(s), and/or one or more application programming interfaces (APIs), which may be implemented to facilitate or perform the features, functions, or other disclosure described herein, such as any methods, processes, elements or limitations, as illustrated, depicted, or described for the various flowcharts, illustrations, diagrams, figures, and/or other disclosure herein. For example, at least some of the applications, software components, or APIs may be, include, otherwise be part of, an imaging based machine learning model or component, such as the trapped hair model 108, where each may be configured to facilitate their various functionalities discussed herein. It should be appreciated that one or more other applications may be envisioned and that are executed by the processor(s) 104.

The processor(s) 104 may be connected to the memories 106 via a computer bus responsible for transmitting electronic data, data packets, or otherwise electronic signals to and from the processor(s) 104 and memories 106 in order to implement or perform the machine readable instructions, methods, processes, elements or limitations, as illustrated, depicted, or described for the various flowcharts, illustrations, diagrams, figures, and/or other disclosure herein.

The processor(s) 104 may interface with the memory 106 via the computer bus to execute the operating system (OS). The processor(s) 104 may also interface with the memory 106 via the computer bus to create, read, update, delete, or otherwise access or interact with the data stored in the memories 106 and/or the database 104 (e.g., a relational database, such as Oracle, DB2, MySQL, or a NoSQL based database, such as MongoDB). The data stored in the memories 106 and/or the database 105 may include all or part of any of the data or information described herein, including, for example, training images and/or user images (e.g., either of which including any one or more of images 202*a*, 202*b*, and/or 202*c*) or other information of the user, including demographic, age, race, skin type, or the like.

The imaging server(s) 102 may further include a communication component configured to communicate (e.g., send and receive) data via one or more external/network port(s) to one or more networks or local terminals, such as computer network 120 and/or terminal 109 (for rendering or visualizing) described herein. In some embodiments, imaging server(s) 102 may include a client-server platform technology such as ASP.NET, Java J2EE, Ruby on Rails, Node.js, a web service or online API, responsive for receiving and responding to electronic requests. The imaging server(s) 102 may implement the client-server platform technology that may interact, via the computer bus, with the memories(s) 106 (including the applications(s), component(s), API(s), data, etc. stored therein) and/or database 105 to implement or perform the machine readable instructions, methods, processes, elements or limitations, as illustrated, depicted, or described for the various flowcharts, illustrations, diagrams, figures, and/or other disclosure herein. According to some embodiments, the imaging server(s) 102 may include, or interact with, one or more transceivers (e.g., WWAN, WLAN, and/or WPAN transceivers) functioning in accordance with IEEE standards, 3GPP standards, or other standards, and that may be used in receipt and transmission of data via external/network ports connected to computer network 120. In some embodiments, computer network 120 may comprise a private network or local area network (LAN). Additionally, or alternatively, computer network 120 may comprise a public network such as the Internet.

Imaging server(s) 102 may further include or implement an operator interface configured to present information to an administrator or operator and/or receive inputs from the administrator or operator. As shown in FIG. 1, an operator interface may provide a display screen (e.g., via terminal 109). Imaging server(s) 102 may also provide I/O components (e.g., ports, capacitive or resistive touch sensitive input panels, keys, buttons, lights, LEDs), which may be directly accessible via or attached to imaging server(s) 102 or may be indirectly accessible via or attached to terminal 109. According to some embodiments, an administrator or operator may access the server 102 via terminal 109 to review information, make changes, input training data or images, and/or perform other functions.

As described above herein, in some embodiments, imaging server(s) 102 may perform the functionalities as discussed herein as part of a "cloud" network or may otherwise communicate with other hardware or software components within the cloud to send, retrieve, or otherwise analyze data or information described herein.

In general, a computer program or computer based product, application, or code (e.g., the model(s), such as AI models, or other computing instructions described herein) may be stored on a computer usable storage medium, or tangible, non-transitory computer-readable medium (e.g., standard random access memory (RAM), an optical disc, a universal serial bus (USB) drive, or the like) having such computer-readable program code or computer instructions embodied therein, wherein the computer-readable program code or computer instructions may be installed on or otherwise adapted to be executed by the processor(s) 104 (e.g., working in connection with the respective operating system in memories 106) to facilitate, implement, or perform the machine readable instructions, methods, processes, elements or limitations, as illustrated, depicted, or described for the various flowcharts, illustrations, diagrams, figures, and/or other disclosure herein. In this regard, the program code may be implemented in any desired program language, and may be implemented as machine code, assembly code, byte code, interpretable source code or the like (e.g., via Golang, Python, C, C++, C#, Objective-C, Java, Scala, ActionScript, JavaScript, HTML, CSS, XML, etc.).

As shown in FIG. 1, imaging server(s) 102 are communicatively connected, via computer network 120 to the one or more user computing devices 111$c$1-111$c$3 and/or 112$c$1-112$c$3 via base stations 111$b$ and 112$b$. In some embodiments, base stations 111$b$ and 112$b$ may comprise cellular base stations, such as cell towers, communicating to the one or more user computing devices 111$c$1-111$c$3 and 112$c$1-112$c$3 via wireless communications 121 based on any one or more of various mobile phone standards, including NMT, GSM, CDMA, UMMTS, LTE, 5G, or the like. Additionally or alternatively, base stations 111$b$ and 112$b$ may comprise routers, wireless switches, or other such wireless connection points communicating to the one or more user computing devices 111$c$1-111$c$3 and 112$c$1-112$c$3 via wireless communications 122 based on any one or more of various wireless standards, including by non-limiting example, IEEE 802.11a/b/c/g (WIFI), the BLUETOOTH standard, or the like.

Any of the one or more user computing devices 111$c$1-111$c$3 and/or 112$c$1-112$c$3 may comprise mobile devices and/or client devices for accessing and/or communications with imaging server(s) 102. In various embodiments, user computing devices 111$c$1-111$c$3 and/or 112$c$1-112$c$3 may comprise a cellular phone, a mobile phone, a tablet device, a personal data assistance (PDA), or the like, including, by non-limiting example, an APPLE iPhone or iPad device or a GOOGLE ANDROID based mobile phone or tablet.

Moreover, in various embodiments, user computing devices 111$c$1-111$c$3 and/or 112$c$1-112$c$3 may comprise a home or personal assistant, including, for example GOOGLE HOME, AMAZON ALEXA, an ECHO SHOW device, or the like.

In additional embodiments, user computing devices 111$c$1-111$c$3 and/or 112$c$1-112$c$3 may comprise a retail computing device. A retail computing device would be configured in the same or similar manner, e.g., as described herein for user computing devices 111$c$1-111$c$3, including having a processor and memory, for implementing, or communicating with (e.g., via server(s) 102), a trapped hair model 108 as described herein. However, a retail computing device may be located, installed, or otherwise positioned within a retail environment to allow users and/or customers of the retail environment to utilize the digital imaging systems and methods on site within the retail environment. For example, the retail computing device may be installed within a kiosk for access by a user. The user may then upload or transfer images (e.g., from a user mobile device) to the kiosk to implement the digital imaging systems and methods described herein. Additionally, or alternatively, the kiosk may be configured with a camera to allow the user to take new images (e.g., in a private manner where warranted) of himself or herself for upload and transfer. In such embodiments, the user or consumer himself or herself would be able to use the retail computing device to receive and/or have rendered a user-specific electronic recommendation, as described herein, on a display screen of the retail computing device. Additionally, or alternatively, the retail computing device may be a mobile device (as described herein) as carried by an employee or other personnel of the retail environment for interacting with users or consumers on site. In such embodiments, a user or consumer may be able to interact with an employee or otherwise personnel of the retail environment, via the retail computing device (e.g., by transferring images from a mobile device of the user to the retail computing device or by capturing new images by a camera of the retail computing device), to receive and/or have rendered a user-specific electronic recommendation, as described herein, on a display screen of the retail computing device.

In addition, the one or more user computing devices 111$c$1-111$c$3 and/or 112$c$1-112$c$3 may implement or execute an operating system (OS) or mobile platform such as Apple's iOS and/or Google's Android operation system. Any of the one or more user computing devices 111$c$1-111$c$3 and/or 112$c$1-112$c$3 may comprise one or more processors and/or one or more memories for storing, implementing, or executing computing instructions or code, e.g., a mobile application, as described in various embodiments herein. As shown in FIG. 1, the trapped hair model 108 may also be stored locally on a memory of a user computing device (e.g., user computing device 111$c$1).

User computing devices 111$c$1-111$c$3 and/or 112$c$1-112$c$3 may comprise a wireless transceiver to receive and transmit wireless communications 121 and/or 122 to and from base stations 111$b$ and/or 112$b$. Pixel based images 202$a$, 202$b$, and/or 202$c$ may be transmitted via computer network 120 to imaging server(s) 102 for training of model(s) and/or imaging analysis as describe herein.

In addition, the one or more user computing devices 111$c$1-111$c$3 and/or 112$c$1-112$c$3 may include a digital camera and/or digital video camera for capturing or taking digital images and/or frames (e.g., which can be any one or more of images 202$a$, 202$b$, and/or 202$c$). Each digital image may comprise pixel data for training or implementing model(s), such as AI or machine learning models, as described herein. For example, a digital camera and/or digital video camera of, e.g., any of user computing devices 111c1-111c3 and/or 112c1-112c3 may be configured to take, capture, or otherwise generate digital images (e.g., pixel based images 202a, 202b, and/or 202c) and, at least in some embodiments, may store such images in a memory of a respective user computing devices.

Still further, each of the one or more user computer devices 111c1-111c3 and/or 112c1-112c3 may include a display screen for displaying graphics, images, text, product recommendations, data, pixels, features, and/or other such visualizations or information as described herein. In various embodiments, graphics, images, text, product recommendations, data, pixels, features, and/or other such visualizations or information may be received by imaging server(s) 102 for display on the display screen of any one or more of user computer devices 111c1-111c3 and/or 112c1-112c3. Additionally, or alternatively, a user computer device may comprise, implement, have access to, render, or otherwise expose, at least in part, an interface or a guided user interface (GUI) for displaying text and/or images on its display screen.

FIGS. 2A-2C illustrate example images 202a, 202b, and 202c that may be collected or aggregated at imaging server(s) 102 and may be analyzed by, and/or used to train, a trapped hair model (e.g., an AI model such as a machine learning imaging model as described herein). Each of these images may comprise pixel data (e.g., RGB data) representing feature data and corresponding to each of the personal attributes of the respective users 202au, 202bu, and 202cu, within the respective image. The pixel data may be captured by a digital camera of one of the user computing devices (e.g., one or more user computer devices 111c1-111c3 and/or 112c1-112c3).

Generally, as described herein, pixel data (e.g., pixel data 202ap, 202bp, and/or 202cp) comprises individual points or squares of data within an image, where each point or square represents a single pixel (e.g., pixel 202ap1 and pixel 202ap2) within an image. Each pixel may be a specific location within an image. In addition, each pixel may have a specific color (or lack thereof). Pixel color may be determined by a color format and related channel data associated with a given pixel. For example, a popular color format includes the red-green-blue (RGB) format having red, green, and blue channels. That is, in the RGB format, data of a pixel is represented by three numerical RGB components (Red, Green, Blue), that may be referred to as channel data, to manipulate the color of pixel's area within the image. In some implementations, the three RGB components may be represented as three 8-bit numbers for each pixel. Three 8-bit bytes (one byte for each of RGB) is used to generate 24 bit color. Each 8-bit RGB component can have 256 possible values, ranging from 0 to 255 (i.e., in the base 2 binary system, an 8 bit byte can contain one of 256 numeric values ranging from 0 to 255). This channel data (R, G, and B) can be assigned a value from 0 255 and be used to set the pixel's color. For example, three values like (250, 165, 0), meaning (Red=250, Green=165, Blue=0), can denote one Orange pixel. As a further example, (Red=255, Green=255, Blue=0) means Red and Green, each fully saturated (255 is as bright as 8 bits can be), with no Blue (zero), with the resulting color being Yellow. As a still further example, the color black has an RGB value of (Red=0, Green=0, Blue=0) and white has an RGB value of (Red=255, Green=255, Blue=255). Gray has the property of having equal or similar RGB values. So (Red=220, Green=220, Blue=220) is a light gray (near white), and (Red=40, Green=40, Blue=40) is a dark gray (near black).

In this way, the composite of three RGB values creates the final color for a given pixel. With a 24-bit RGB color image using 3 bytes there can be 256 shades of red, and 256 shades of green, and 256 shades of blue. This provides 256×256×256, i.e., 16.7 million possible combinations or colors for 24 bit RGB color images. In this way, the pixel's RGB data value shows how much of each of Red, and Green, and Blue comprise the pixel. The three colors and intensity levels are combined at that image pixel, i.e., at that pixel location on a display screen, to illuminate a display screen at that location with that color. In is to be understood, however, that other bit sizes, having fewer or more bits, e.g., 10-bits, may be used to result in fewer or more overall colors and ranges.

As a whole, the various pixels, positioned together in a grid pattern, form a digital image (e.g., pixel data 202ap, 202bp, and/or 202cp). A single digital image can comprise thousands or millions of pixels. Images can be captured, generated, stored, and/or transmitted in a number of formats, such as JPEG, TIFF, PNG and GIF. These formats use pixels to store represent the image.

FIG. 2A illustrates an example image 202a and its related pixel data (e.g., pixel data 202ap) that may be used for training and/or implementing a trapped hair model (e.g., trapped hair model 108), in accordance with various embodiments disclosed herein. Example image 202a illustrates a user 202au or individual before removing hair from a body area location comprising the user's cheek. Image 202a is comprised of pixel data, including pixel data 202ap. Pixel data 202ap includes a plurality of pixels including pixel 202ap1 and pixel 202ap2. Pixel 202ap1 is a red toned pixel positioned in image 202a indicative of a bump associated a trapped or ingrown hair of the user 202au before the user 202au has removed hair from his cheek. Pixel 202ap2 is a pixel positioned in image 202a comprising an area of the cheek of the user 202au without any trapped or ingrown hair. Pixel data 202ap includes various remaining pixels including portions of the cheek of the user 202au with or without trapped or ingrown hairs, and other features as shown in FIG. 2A.

FIG. 2B illustrates an example image 202b and its related pixel data (e.g., pixel data 202bp) that may be used for training and/or implementing a trapped hair model (e.g., trapped hair model 108), in accordance with various embodiments disclosed herein. Example image 202b illustrates a user 202bu or individual before removing hair from a body area location comprising the user's underarm. Image 202b is comprised of pixel data, including pixel data 202bp. Pixel data 202bp includes a plurality of pixels including pixel 202bp1 and pixel 202bp2. Pixel 202bp1 is a red toned pixel positioned in image 202b indicative of a bump associated with a trapped or ingrown hair on the underarm of the user 202bu before the user 202bu has removed hair from her underarm. Pixel 202bp2 is a pixel positioned in image 202b comprising an area of the underarm of the user 202bu without any trapped or ingrown hairs. Pixel data 202bp includes various remaining pixels including portions of the underarm of the user 202bu with or without trapped or ingrown hair before hair removal, and other features as shown in FIG. 2B.

FIG. 2C illustrates an example image 202c and its related pixel data (e.g., pixel data 202cp) that may be used for training and/or implementing a trapped hair model (e.g., trapped hair model 108), in accordance with various embodiments disclosed herein. Example image 202c illustrates a user 202cu or individual before removing hair from a body area location comprising the user's leg. Image 202c is comprised of pixel data, including pixel data 202cp. Pixel data 202cp includes a plurality of pixels including pixel 202cp1 and pixel 202cp2. Pixel 202cp1 is a red toned pixel (e.g., a pixel with low R, G, and B values) positioned in image 202c indicative of a bump associated with a trapped or ingrown hair on the leg of the user 202cu before the user 202cu has removed hair from her leg. Pixel 202cp2 is a pixel positioned in image 202c comprising an area of the leg of the user 202cu without trapped or ingrown hairs. Pixel data 202cp includes various remaining pixels including portions of the leg of the user 202cu with or without trapped or ingrown hair before hair removal, and other features as shown in FIG. 2C.

Figure 3:
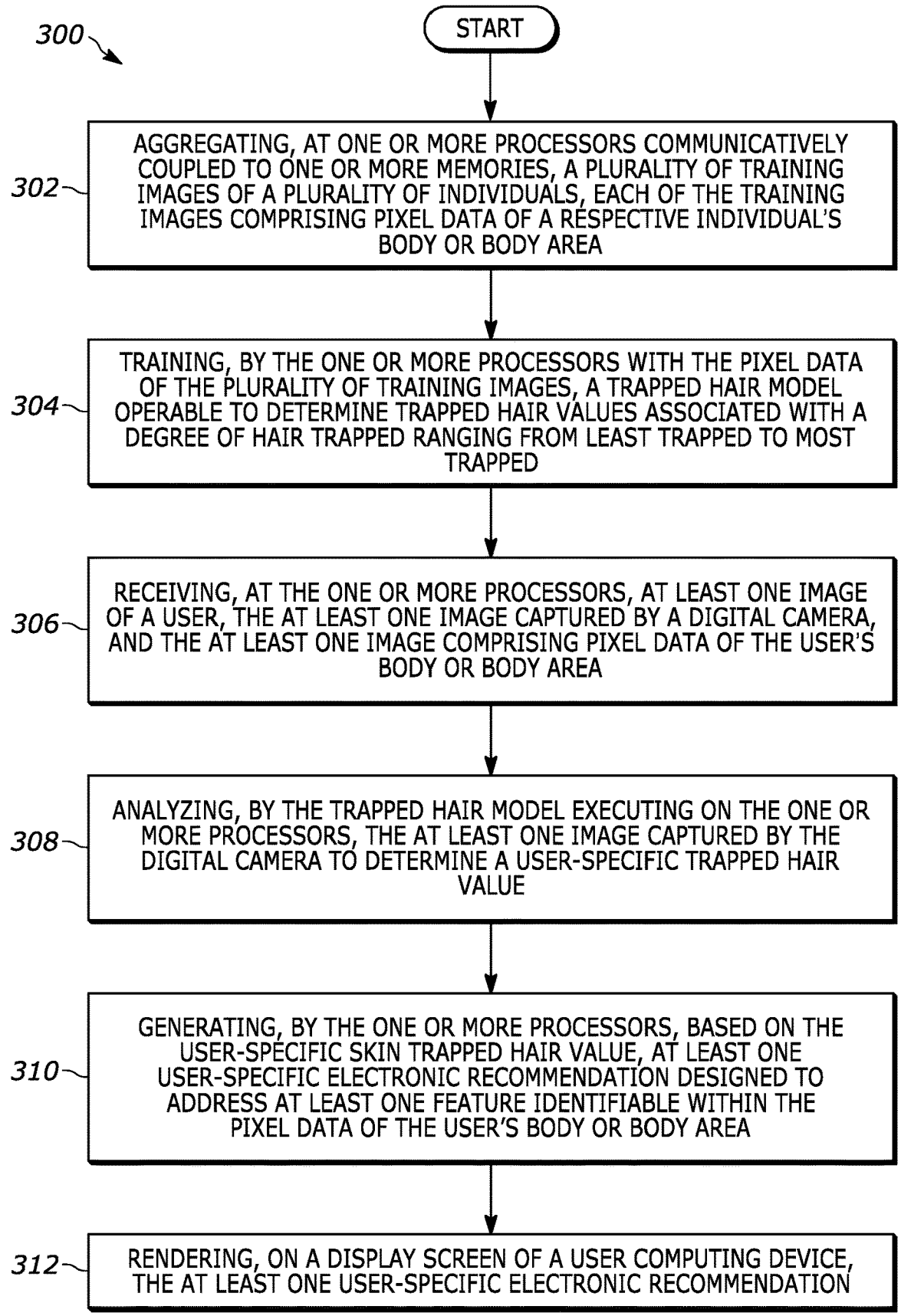
FIG. 3 illustrates a diagram of a digital imaging method of analyzing pixel data of an image of a user's body before removing hair for determining a trapped hair value, in accordance with various embodiments disclosed herein.

FIG. 3 illustrates a diagram of a digital imaging method 300 of analyzing pixel data of an image (e.g., images 202a, 202b, and/or 202c) of a user's body before removing hair for determining a trapped hair value, in accordance with various embodiments disclosed herein. Images, as described herein, are generally pixel images as captured by a digital camera (e.g., a digital camera of user computing device 111c1). In some embodiments an image may comprise or refer to a plurality of images such as a plurality of images (e.g., frames) as collected using a digital video camera. Frames comprise consecutive images defining motion, and can comprise a movie, a video, or the like.

At block 302, the method 300 comprises aggregating, at one or more processors communicatively coupled to one or more memories, a plurality of training images of a plurality of individuals before removing hair, each of the training images comprising pixel data of a respective individual's body or body area before removing hair (e.g., using a wet razor, a dry shaver, an epilator, a wax, etc.). In some examples, each of the training images may be captured within a threshold timeframe prior to each respective individual's hair removal (e.g., within one hour prior to hair removal, within six hours prior to hair removal, within twelve hours prior to hair removal, etc.). For instance, in some examples, the one or more processors include at least one of a server or a cloud-based computing platform, and the server or the cloud-based computing platform receives the plurality of training images of the plurality of individuals via a computer network.

At block 304, the method 300 comprises training, by the one or more processors with the pixel data of the plurality of training images, a trapped hair model (e.g., trapped hair model 108) operable to determine trapped hair values associated with a degree of trapped hair ranging from least trapped or ingrown hair to most trapped or ingrown hair. In various embodiments, the trapped hair model is an artificial intelligence (AI) based model trained with at least one AI algorithm.

In some examples, the hair removal value may be a scaled value. The trapped hair scale can be an internalized scale or otherwise custom scale, unique to the trapped hair model, where a least or small trapped hair value may be determined from an image or set of images having skin areas with low trapped hair values, i.e., images where the pixel data indicates lower values for the number of trapped or ingrown hairs before hair removal, and/or a lower severity level of any trapped or ingrown hairs before hair removal. Similarly, a most or large trapped hair value may be determined from an image or set of images having body areas with high trapped hair values, i.e., images where the pixel data indicates that the user's body or body area has a higher number of trapped or ingrown hairs before hair removal, and/or a higher severity level of any trapped or ingrown before hair removal.

In some embodiments, the trapped hair scale may be a percentage scale, e.g., outputting trapped hair values from 0% to 100%, where 0% represents least trapped or ingrown hairs and 100% represents most trapped or ingrown hairs. Values can range across this scale where a trapped hair value of 67% represents one or more pixels of a skin area detected within an image that has a higher trapped hair value than a trapped hair value of 10% as detected for one or more pixels of a body or body area within the same image or a different image (of the same or different user).

In some embodiments, the trapped hair scale may be a numerical or decimal based scale, e.g., outputting trapped hair values, e.g., from 0 to 10, where 0 represents least trapped or ingrown hairs and 10 represents most trapped or ingrown hairs. Values can range across this scale where a trapped hair value of 7 represents one or more pixels of a skin area detected within an image that has a higher trapped hair value than a trapped hair value of 2 as detected for one or more pixels of a body or body area within the same image or a different image (of the same or different user).

Trapped hair values may be determined at the pixel level or for a given body area (e.g., one or more pixels) in an image.

In some embodiments, a comprehensive trapped hair value, which can be a user-specific trapped hair value as described herein, may be determined by averaging (or otherwise statistically analyzing) trapped hair values for one or more pixels of a given body area.

In some examples, the server or the cloud-based computing platform discussed above with respect to block 302 trains the trapped hair model with the pixel data of the plurality of training images.

Training of the trapped hair model 108 involves image analysis of the training images to configure weights of trapped hair model, and its underlying algorithm (e.g., machine learning or artificial intelligence algorithm) used to predict and/or classify future images. For example, in various embodiments herein, generation of trapped hair model 108 involves training trapped hair model 108 with the plurality of training images of a plurality of individuals, where each of the training images comprise pixel data of the user's body or body area before removing hair. In some embodiments, one or more processors of a server or a cloud-based computing platform (e.g., imaging server(s) 102) may receive the plurality of training images of the plurality of individuals via a computer network (e.g., computer network 120). In such embodiments, the server and/or the cloud-based computing platform may train the trapped hair model 108 with the pixel data of the plurality of training images.

For example, in various embodiments, a machine learning imaging model as described herein (e.g. trapped hair model 108), may be trained using a supervised or unsupervised machine learning program or algorithm. The machine learning program or algorithm may employ a neural network, which may be a convolutional neural network, a deep learning neural network, or a combined learning module or program that learns in two or more features or feature datasets (e.g., pixel data) in a particular areas of interest. The machine learning programs or algorithms may also include natural language processing, semantic analysis, automatic reasoning, regression analysis, support vector machine (SVM) analysis, decision tree analysis, random forest analysis, K-Nearest neighbor analysis, naïve Bayes analysis, clustering, reinforcement learning, and/or other machine learning algorithms and/or techniques. In some embodiments, the artificial intelligence and/or machine learning based algorithms may be included as a library or package executed on server(s) 102. For example, libraries may include the TENSORFLOW based library, the PYTORCH library, and/or the SCIKIT-LEARN Python library.

Machine learning may involve identifying and recognizing patterns in existing data (such as training a model based on pixel data within images having pixel data of respective individuals' bodies before removing hair) in order to facilitate making predictions or identification for subsequent data (such as using the model on new pixel data of a new individual's body before removing hair in order to determine a user-specific trapped hair value).

Machine learning model(s), such as the trapped hair model described herein for some embodiments, may be created and trained based upon example data (e.g., "training data" and related pixel data) inputs or data (which may be termed "features" and "labels") in order to make valid and reliable predictions for new inputs, such as testing level or production level data or inputs. In supervised machine learning, a machine learning program operating on a server, computing device, or otherwise processor(s), may be provided with example inputs (e.g., "features") and their associated, or observed, outputs (e.g., "labels") in order for the machine learning program or algorithm to determine or discover rules, relationships, patterns, or otherwise machine learning "models" that map such inputs (e.g., "features") to the outputs (e.g., labels), for example, by determining and/or assigning weights or other metrics to the model across its various feature categories. Such rules, relationships, or otherwise models may then be provided subsequent inputs in order for the model, executing on the server, computing device, or otherwise processor(s), to predict, based on the discovered rules, relationships, or model, an expected output.

In unsupervised machine learning, the server, computing device, or otherwise processor(s), may be required to find its own structure in unlabeled example inputs, where, for example multiple training iterations are executed by the server, computing device, or otherwise processor(s) to train multiple generations of models until a satisfactory model, e.g., a model that provides sufficient prediction accuracy when given test level or production level data or inputs, is generated. The disclosures herein may use one or both of such supervised or unsupervised machine learning techniques.

Image analysis may include training a machine learning based model (e.g., the trapped hair model 108) on pixel data of images of one or more individuals' bodies before removing hair. Additionally, or alternatively, image analysis may include using a machine learning imaging model, as previously trained, to determine, based on the pixel data (e.g., including their RGB values) of one or more images of the body of the individual(s) before removing hair, a user-specific trapped hair value before removing hair. The weights of the model may be trained via analysis of various RGB values of individual pixels of a given image. For example, red toned RGB values (e.g., a pixel with values R=215, G=90, B=85) may indicate areas of the user's body having red bumps associated with trapped or ingrown hairs, as well as the number or severity of any trapped or ingrown hairs of the user's body. Lighter RGB values (e.g., a pixel with R=181, G=170, and B=191) may indicate a lighter value, such as a skin tone color, i.e., indicating areas of the user's body without trapped hairs. As another example, RGB values of pixels within a given image may be analyzed to determine a "baseline" RGB value or a "baseline" RGB range indicative of the skin tone of the user. Pixels darker than the baseline RGB range, or darker than the baseline RGB value by a threshold degree, may be pixels indicative of areas of the user's skin that are more pigmented due to trapped hair or other skin irritants. When a large number of pixels having red toned RGB values (or RGB values darker than the baseline RGB value or range) are positioned within a given image of an area of the user's body before removing hair, this may indicate that the user is experiencing a large number of trapped or ingrown hairs in the area of the user's body shown in the image. In this way, pixel data (e.g., detailing one or more features of an individual, such as the user's body or body area before removing hair) of 10,000s of training images may be used to train or use a machine learning imaging model to determine a user-specific trapped hair value before removing hair.

In various embodiments, a trapped hair model (e.g., trapped hair model 108) may be further trained, by one or more processors (e.g., imaging server(s) 102), with the pixel data of the plurality of training images, to output one or more location identifiers indicating one or more corresponding body area locations of respective individuals. In such embodiments, the trapped hair model (e.g., trapped hair model 108), executing on the one or more processors (e.g., imaging server(s) 102) and analyzing the at least one image of the user, can determine a location identifier indicating a body area location of the user's body or body area. For example, body area locations may comprise a user's face, a user's cheek, a user's neck, a user's head, a user's groin, a user's underarm, a user's chest, a user's back, a user's leg, a user's arm, or a user's bikini area. For example, each of images image 202a, 202b, and 202 illustrate example body area locations including a user's cheek, a user's underarm or armpit, and a user's leg, respectively.

With reference to FIG. 3, at block 306, the method 300 comprises receiving, at the one or more processors (e.g., imaging server(s) 102 and/or a user computing device, such as user computing device 111c1), at least one image of a user. The at least one image may have been captured by a digital camera. In addition, the at least one image may comprise pixel data of the user's body or body area before removing hair (e.g., using a wet razor, a dry shaver, an epilator, a wax, etc.). In some examples, each of the training images may be captured within a threshold timeframe prior to each respective individual's hair removal (e.g., within one hour prior to hair removal, within six hours prior to hair removal, within twelve hours prior to hair removal, etc.). In some examples, the digital camera is a digital video camera, and the at least one image is a plurality of images. In some examples, the server or a cloud-based computing platform discussed above with respect to block 302 receives the at least one image. Moreover, in some examples, a user computing device (e.g., a mobile device, a tablet, a handheld device, a desktop device, a personal assistant device, a home assistant device, a retail device, etc.) receives the at least one image.

At block 308, the method 300 comprises analyzing, by the trapped hair model (e.g., trapped hair model 108) executing on the one or more processors (e.g., imaging server(s) 102 and/or a user computing device, such as user computing device 111c1), the at least one image captured by the digital camera to determine a user-specific trapped hair value (e.g., based on a number or severity level of trapped or ingrown hairs). In some examples, the server or a cloud-based computing platform discussed above with respect to block 302 analyzes the at least one image to determine the user-specific trapped hair value. Furthermore, in some examples, the user computing device discussed above with respect to block 306 analyzes the at least one image to determine the user-specific trapped hair value. Additionally, in some examples, the trapped hair model 108 may further analyze the at least one image captured by the digital camera to determine a location identifier indicating a body area location of the user's body or body area (e.g., one of the user's face, the user's cheek, the user's neck, the user's jaw, the user's head, the user's groin, the user's underarm, the user's chest, the user's back, the user's leg, the user's arm, the user's bikini area, etc.).

At block 310, the method 300 comprises generating, by the one or more processors (e.g., imaging server(s) 102 and/or a user computing device, such as user computing device 111c1), based on the user-specific trapped hair value, at least one user-specific electronic recommendation designed to address at least one feature identifiable within the pixel data of the user's body or body area. Moreover, in some examples, the server or a cloud-based computing platform discussed above with respect to block 302 generates the at least one user-specific recommendation and transmits the user-specific recommendation to the user computing device for rendering on the display screen of the user computing device. Furthermore, in some examples, the user computing device discussed above with respect to block 306 generates the at least one user-specific recommendation.

For instance, the user-specific recommendation may include at least one product recommendation for a manufactured product designed to address at least one feature identifiable within the pixel data of the user's body or body area. As another example, the user-specific recommendation may include a recommended shaving behavior, e.g., selected from two or more available behaviors based on the trapped hair value.

At block 312, the method 300 comprises rendering, on a display screen of the user computing device, the at least one user-specific recommendation. A user computing device may comprise at least one of a mobile device, a tablet, a handheld device, a desktop device, a personal assistant device, a home assistant device, or a retail device, for example, as described herein for FIG. 1. In some embodiments, the user computing device (e.g., user computing device 111c1) may receive the at least one image comprising the pixel data of the user's body or body area. In such embodiments, the user computing device may execute the trapped hair model (e.g., trapped hair model 108) locally and generate, based on output of the trapped hair model (e.g., trapped hair model 108), the user-specific recommendation. The user computing device 111c1 may then render the user-specific recommendation on its display screen.

Additionally, or alternatively, in other embodiments, the imaging server(s) 102 may analyze the user image remotely from the user computing device to determine the user-specific trapped hair value and/or user-specific electronic recommendation designed to address at least one feature identifiable within the pixel data comprising the user's body or body area. For example, in such embodiments imaging server or a cloud-based computing platform (e.g., imaging server(s) 102) receives, across computer network 120, the at least one image comprising the pixel data of at the user's body or body area. The server or a cloud-based computing platform may then execute the trapped hair model (e.g., trapped hair model 108) and generate, based on output of the trapped hair model (e.g., trapped hair model 108), the user-specific recommendation. The server or a cloud-based computing platform may then transmit, via the computer network (e.g., computer network 120), the user-specific recommendation to the user computing device for rendering on the display screen of the user computing device.

In some embodiments, the user may submit a new image to the trapped hair model for analysis as described herein. In such embodiments, one or more processors (e.g., imaging server(s) 102 and/or a user computing device, such as user computing device 111c1) may receive a new image of the user before removing hair. The new image may be captured by a digital camera of user computing device 111c1. The new image may comprise pixel data of at least a portion of the user's body or body area. The trapped hair model (e.g., trapped hair model 108) may then analyze, on the one or more processors (e.g., imaging server(s) 102 and/or a user computing device, such as user computing device 111c1), the new image captured by the digital camera to determine a new user-specific trapped hair value before removing hair. In some examples, the one or more processors may generate a delta trapped hair value based on a comparison between the new user-specific trapped hair value and the (initial or previous) trapped hair value. A new user-specific electronic recommendation or comment may be generated, based on the new user-specific trapped hair value or based on the delta trapped hair value, regarding at least one feature identifiable within the pixel data of the new image. The new user-specific recommendation or comment (e.g., message) may then be rendered on a display screen of a user computing device of the user.

In some embodiments, a user-specific electronic recommendation may be displayed on the display screen of a user computing device (e.g., user computing device 111c1) with a graphical representation of the user's body or body area as annotated with one or more graphics or textual renderings corresponding to the user-specific trapped hair value. In still further embodiments, the at least one user-specific electronic recommendation may be rendered in real-time or near-real time during hair removal.

In additional embodiments, a user-specific electronic recommendation may comprise a product recommendation for a manufactured product. In such embodiments, the user-specific electronic recommendation may be displayed on the display screen of a user computing device (e.g., user computing device 111c1) with instructions (e.g., a message) for treating, with the manufactured product, the at least one feature identifiable the pixel data comprising the at least the portion of the user's body or body area. In still further embodiments, either the user computing device 111c1 and/or imaging server(s) may initiate, based on the product recommendation, the manufactured product for shipment to the user.

Moreover, in some embodiments, a modified image of how the user's body or body area is predicted to appear after treating the at least one feature with the manufactured product may be generated and rendered on the display screen of the user computing device 111c1, e.g., alongside the electronic recommendation for the manufactured product. For instance, the modified image may depict a reduction in the number and/or the severity of trapped hairs that the user would be expected to experience after treating the at least one feature with the manufactured product.

Figure 4:
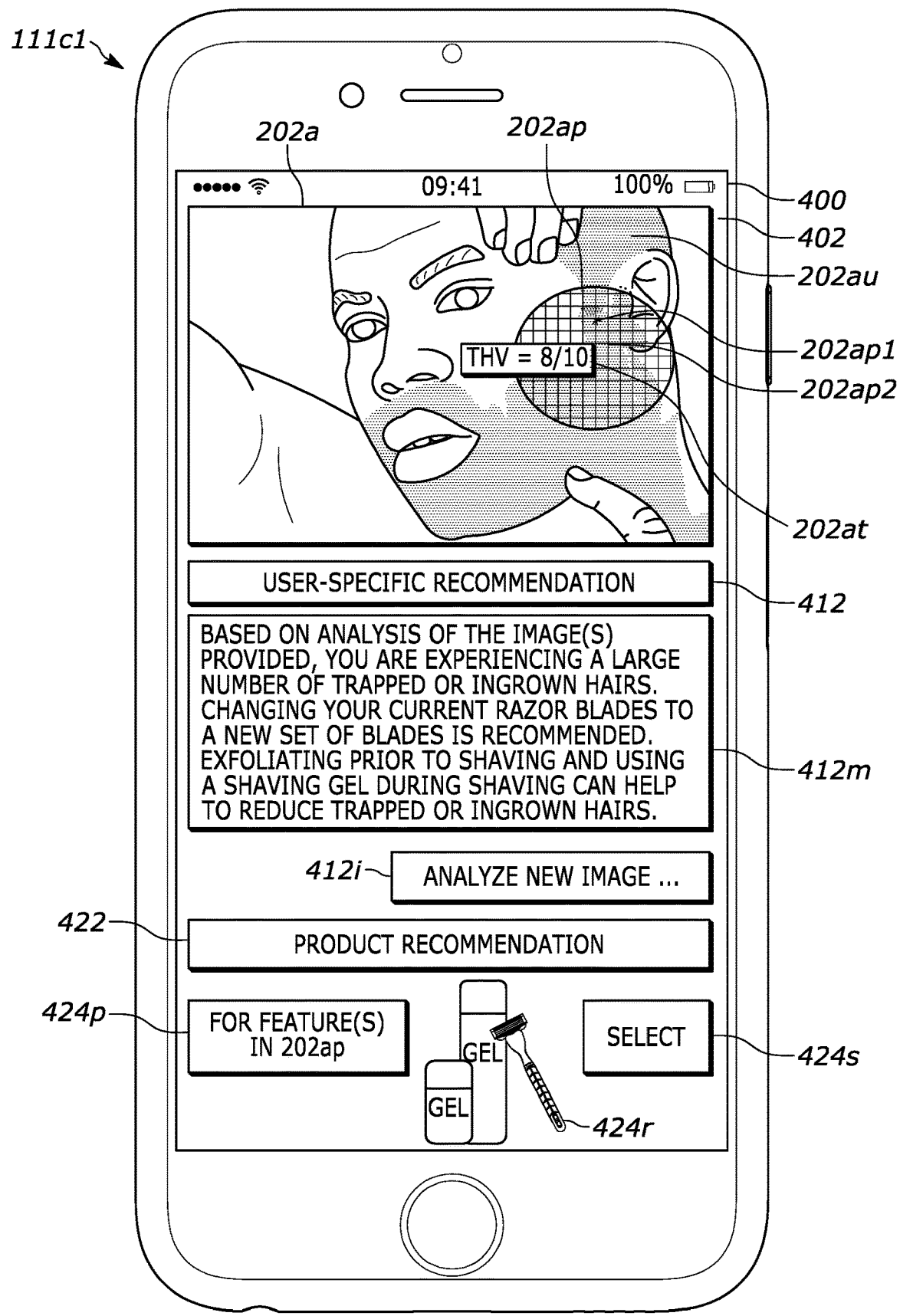
FIG. 4 illustrates an example user interface as rendered on a display screen of a user computing device in accordance with various embodiments disclosed herein.

FIG. 4 illustrates an example user interface 402 as rendered on a display screen 400 of a user computing device 111c1 in accordance with various embodiments disclosed herein. For example, as shown in the example of FIG. 4, user interface 402 may be implemented or rendered via an application (app) executing on user computing device 111c1.

For example, as shown in the example of FIG. 4, user interface 402 may be implemented or rendered via a native app executing on user computing device 111c1. In the example of FIG. 4, user computing device 111c1 is a user computer device as described for FIG. 1, e.g., where 111c1 is illustrated as an APPLE iPhone that implements the APPLE iOS operating system and has display screen 400. User computing device 111c1 may execute one or more native applications (apps) on its operating system. Such native apps may be implemented or coded (e.g., as computing instructions) in a computing language (e.g., SWIFT) executable by the user computing device operating system (e.g., APPLE iOS) by the processor of user computing device 111c1.

Additionally, or alternatively, user interface 402 may be implemented or rendered via a web interface, such as via a web browser application, e.g., Safari and/or Google Chrome app(s), or other such web browser or the like.

As shown in the example of FIG. 4, user interface 402 comprises a graphical representation (e.g., image 202a) of the user's skin. Image 202a may be the at least one image the user's body or body area (or graphical representation thereof) before removing hair and as analyzed by the trapped hair model (e.g., trapped hair model 108) as described herein. In the example of FIG. 4, graphical representation (e.g., image 202a) of the user's skin is annotated with one or more graphics (e.g., area of pixel data 202ap) or textual rendering (e.g., text 202at) corresponding to the number or severity of trapped or ingrown hairs experienced by the user before removing hair. For example, the area of pixel data 202ap may be annotated or overlaid on top of the image of the user (e.g., image 202a) to highlight the area or feature(s) identified within the pixel data (e.g., feature data and/or raw pixel data) by the trapped hair model (e.g., trapped hair model 108). In the example of FIG. 4, the area of pixel data 202ap and the feature(s) identified within the pixel data 202ap include the number of trapped or ingrown hairs before hair removal, the severity level of any trapped or ingrown hairs before hair removal, and other features shown in area of pixel data 202ap. In various embodiments, the pixels identified as the specific features indicating trapped or ingrown hairs (e.g., pixel 202ap1 as a red toned pixel indicating a trapped or ingrown hair) may be highlighted or otherwise annotated when rendered.

Textual rendering (e.g., text 202at) shows a user-specific trapped hair value (e.g., 8/10) which illustrates that the user's trapped hair value is above average for typical users (e.g., with 10 corresponding to a maximum trapped hair value, 1 corresponding to a minimum trapped hair value, and 5 corresponding to an average trapped hair value). In particular, 8/10 value indicates that the user's hair removal causes a higher rate of trapped or ingrown hairs, and/or more severe trapped or ingrown hairs, compared to other users. It is to be understood that other textual rendering types or values are contemplated herein, where textual rendering types or values may be rendered, for example, as a range of 1 to 100, as a letter grade, or some other indication of a trapped hair value. Additionally, or alternatively, color values may use and/or overlaid on a graphical representation shown on user interface 402 (e.g., image 202a) to indicate trapped or ingrown hairs.

User interface 402 may also include or render a user-specific electronic recommendation 412. In the embodiment of FIG. 4, user-specific electronic recommendation 412 comprises a message 412m to the user designed to address at least one feature identifiable within the pixel data comprising the portion of the user's skin where hair has been removed. As shown in the example of FIG. 4, message 412m recommends to the user to change his or her current razor blades to a new set of blades, to exfoliate prior to shaving, and to use a shaving gel, to reduce his or her number or severity of trapped or ingrown hairs, and, consequently, his or her trapped hair value. The product recommendation can be correlated to the identified feature within the pixel data, and the user computing device 111c1 and/or server(s) 102 can be instructed to output the product recommendation when the feature (e.g., large number of trapped or ingrown hairs, very severe trapped or ingrown hairs, etc.) is identified.

User interface 402 may also include or render a section for a product recommendation 422 for a manufactured product 424r (e.g., a particular razor, a particular set of blades, a particular wax, a particular epilator, and/or a particular shaving gel or shaving cream). The product recommendation 422 generally corresponds to the user-specific electronic recommendation 412, as described above. For example, in the example of FIG. 4, the user-specific electronic recommendation 412 is displayed on display screen 400 of user computing device 111c1 with instructions (e.g., message 412m) for treating, with the manufactured product 424r (e.g., the particular razor, the particular set of blades, the particular wax, the particular epilator, and/or the particular shaving gel or shaving cream) at least one feature (e.g., the number of trapped or ingrown hairs before removing hair, the severity level of any trapped or ingrown hairs before removing hair, etc., as shown at pixel 202ap1) identifiable from the pixel data (e.g., pixel data 202ap) comprising the body or body area of the user before removing hair.

As shown in FIG. 4, user interface 402 recommends a product (e.g., manufactured product 424r (e.g., the particular razor, the particular wax, the particular epilator, and/or the particular shaving gel or shaving cream) based on the user-specific electronic recommendation 412. In the example of FIG. 4, the output or analysis of image(s) (e.g. image 202a) of the trapped hair model 108, e.g., user-specific electronic recommendation 412 and/or its related values (e.g., trapped hair value of 8/10) or related pixel data (e.g., 202ap1 and/or 202ap2) may be used to generate or identify recommendations for corresponding product(s). Such recommendations may include products such as the particular razor, the particular set of blades, the particular wax, the particular epilator, and/or the particular shaving gel or shaving cream, or the like to address the user-specific issue as detected within the pixel data by the trapped hair model (e.g., trapped hair model 108).

In the example of FIG. 4, user interface 402 renders or provides a recommended product (e.g., manufactured product 424r) as determined by the trapped hair model (e.g., trapped hair model 108) and its related image analysis of image 202a and its pixel data and various features. In the example of FIG. 4, this indicated and annotated (424p) on user interface 402.

User interface 402 may further include a selectable UI button 424s to allow a user (e.g., the user of image 202a) to select for purchase or shipment the corresponding product (e.g., manufactured product 424r). In some embodiments, selection of selectable UI button 424s a may cause the recommended product(s) to be shipped to the user (e.g., individual 501) and/or may notify a third party that the individual is interested in the product(s). For example, either user computing device 111c1 and/or imaging server(s) 102 may initiate, based on user-specific electronic recommendation 412, the manufactured product 424r (e.g., the particular razor, the particular set of blades, the particular wax, the particular epilator, and/or the particular shaving gel or shaving cream) for shipment to the user. In such embodiments, the product may be packaged and shipped to the user.

In various embodiments, graphical representation (e.g., image 202a), with graphical annotations (e.g., area of pixel data 202ap), textual annotations (e.g., text 202at), and/or user-specific electronic recommendations 412 may be transmitted, via the computer network (e.g., from an imaging server 102 and/or one or more processors) to user computing device 111c1, for rendering on display screen 400. In other embodiments, no transmission to the imaging server of the user's specific image occurs, where the user-specific recommendation (and/or product specific recommendation) may instead be generated locally, by the trapped hair model (e.g., trapped hair model 108) executing and/or implemented on the user's mobile device (e.g., user computing device 111c1) and rendered, by a processor of the mobile device, on display screen 400 of the mobile device (e.g., user computing device 111c1).

In some embodiments, any one or more of graphical representations (e.g., image 202a), with graphical annotations (e.g., area of pixel data 202ap), textual annotations (e.g., text 202at), user-specific electronic recommendation 412, and/or product recommendation 422 may be rendered (e.g., rendered locally on display screen 400) in real-time or near-real time during hair removal. In embodiments where the image is analyzed by imaging server(s) 102, the image may be transmitted and analyzed in real-time or near real-time by imaging server(s) 102.

In some embodiments the user may provide a new image that may be transmitted to imaging server(s) 102 for updating, retraining, or reanalyzing by trapped hair model 108. In other embodiments, a new image that may be locally received on computing device 111c1 and analyzed, by trapped hair model 108, on the computing device 111c1.

In addition, as shown in the example of FIG. 4, the user may select selectable button 412i for reanalyzing (e.g., either locally at computing device 111c1 or remotely at imaging server(s) 102) a new image. Selectable button 412i may cause user interface 402 to prompt the user to attach a new image for analyzing. Imaging server(s) 102 and/or a user computing device such as user computing device 111c1, may receive a new image of the user before removing hair. The new image may be captured by the digital camera. The new image (e.g., just like image 202a) may comprise pixel data of the body or body area of the user before removing hair. The trapped hair model (e.g., trapped hair model 108), executing on the memory of the computing device (e.g., imaging server(s) 102), may analyze the new image captured by the digital camera to determine a new user-specific trapped hair value before the user removes hair again, or removes hair from a different body area. The computing device (e.g., imaging server(s) 102) may generate, based on the new trapped hair value, a new user-specific electronic recommendation or comment regarding at least one feature identifiable within the pixel data of the new image. For example, the new user-specific electronic recommendation may include a new graphical representation including graphics and/or text (e.g., showing a new user-specific trapped hair value, e.g., 4/10). The new user-specific electronic recommendation may include additional recommendations or additional information for the user, e.g., that the user has improved his or her trapped hair value (i.e., reduced the rate or severity of trapped or ingrown hairs resulting from hair removal) as detected with the pixel data of the new image. In various embodiments, the new user-specific recommendation or comment may be transmitted via the computer network to the user computing device of the user for rendering on the display screen of the user computing device. In other embodiments, no transmission to the imaging server of the user's new image occurs, where the new user-specific recommendation (and/or product specific recommendation) may instead be generated locally, by the trapped hair model (e.g., trapped hair model 108) executing and/or implemented on the user's mobile device (e.g., user computing device 111c1) and rendered, by a processor of the mobile device, on a display screen of the mobile device (e.g., user computing device 111c1).

ASPECTS OF THE DISCLOSURE

1. A digital imaging method of analyzing pixel data of at least one image of a user's body for determining a user-specific trapped hair value before removing hair, the digital imaging method comprising the steps of: aggregating, at one or more processors communicatively coupled to one or more memories, a plurality of training images of a plurality of individuals before removing hair, each of the training images comprising pixel data of a respective individual's body or body area before removing hair; training, by the one or more processors, with the pixel data of the plurality of training images, a trapped hair model operable to determine trapped hair values associated with a trapped hair scale ranging from least trapped hair to most trapped hair; receiving, at the one or more processors, at least one image of a user, the at least one image captured by a digital camera, and the at least one image comprising pixel data of the user's body or body area before removing hair; analyzing by the trapped hair model executing on the one or more processors, the at least one image captured by the digital camera to determine a user-specific trapped hair value; generating, by the one or more processors, based on the user-specific trapped hair value, at least one user-specific electronic recommendation designed to address at least one feature identifiable within the pixel data of the user's body or body area; and rendering, on a display screen of a user computing device, the at least one user-specific electronic recommendation.

2. The digital imaging method of aspect 1, wherein the at least one user-specific electronic recommendation is displayed on the display screen of the user computing device with a graphical representation of the user's body or body area as annotated with one or more graphics or textual renderings corresponding to the user-specific trapped hair value.

3. The digital imaging method of any of aspects 1-2, wherein the at least one user-specific electronic recommendation is a recommendation for a manufactured product.

4. The digital imaging method of any of aspects 1-3, wherein the at least one user-specific electronic recommendation is rendered or transmitted for rendering in real-time or near-real time.

5. The digital imaging method of aspect 3, wherein the at least one user-specific electronic recommendation is displayed on the display screen of the user computing device with instructions for treating, with the manufactured product, the at least one feature identifiable within the pixel data of the user's body or body area.

6. The digital imaging method of aspect 4, further comprising: generating, by the one or more processors, a modified image based on the at least one image, the modified image depicting how the user's body or body area is predicted to appear after treating the at least one feature with the manufactured product; and rendering, on the display screen of the user computing device, the modified image.

7. The digital imaging method of any of aspects 3-6, further comprising the steps of: initiating, by the one or more processors, based on the recommendation for the manufactured product, the manufactured product for shipment to the user.

8. The digital imaging method of any of aspects 1-7, wherein the trapped hair model is an artificial intelligence (AI) based model trained with at least one AI algorithm.

9. The digital imaging method of any of aspects 1-8, wherein the trapped hair model is further trained, by the one or more processors, with the pixel data of the plurality of training images, to output one or more location identifiers indicating one or more corresponding body area locations of respective individuals, and wherein the trapped hair model, executing on the one or more processors and analyzing the at least one image of the user, determines a location identifier indicating a body area location of the user's body or body area.

10. The digital imaging method of aspect 9, wherein the body area location comprises the user's face, the user's cheek, the user's neck, the user's jaw, the user's head, the user's groin, the user's underarm, the user's chest, the user's back, the user's leg, the user's arm, or the user's bikini area.

11. The digital imaging method of any of aspects 1-10, wherein the one or more processors comprises at least one of a server or a cloud-based computing platform, and the server or the cloud-based computing platform receives the plurality of training images of the plurality of individuals via a computer network, and wherein the server or the cloud-based computing platform trains the trapped hair model with the pixel data of the plurality of training images.

12. The digital imaging method of any of aspects 1-11, wherein the server or a cloud-based computing platform receives the at least one image comprising the pixel data of the user's body before removing hair, and wherein the server or a cloud-based computing platform executes the trapped hair model and generates, based on output of the trapped hair model, the user-specific recommendation and transmits, via the computer network, the user-specific recommendation to the user computing device for rendering on the display screen of the user computing device.

13. The digital imaging method of any of aspects 1-12, wherein the user computing device comprises a mobile device, a tablet, a handheld device, a desktop device, a personal assistant device, a home assistant device, or a retail device.

14. The digital imaging method of any of aspects 1-13, wherein the user computing device receives the at least one image comprising the pixel data of the at least a portion of the user's body before removing hair, and wherein the user computing device executes the trapped hair model and generates, based on output of the trapped hair model, the user-specific recommendation, and renders the user-specific recommendation on the display screen of the user computing device.

15. The digital imaging method of any of aspects 1-14, wherein the user-specific recommendation includes a recommended of a behavior selected, by the one or more processors, from at least two available behaviors based upon the trapped hair value.

16. The digital method of any of aspects 1-15, further comprising: receiving, at the one or more processors, a new image of the user, the new image captured by the digital camera, and the new image comprising pixel data of the user's body at a body area location before removing hair; analyzing, by the trapped hair model executing on the one or more processors, the new image captured by the digital camera to determine a new user-specific trapped hair value; generating, based on the new user-specific trapped hair value, a new user-specific electronic recommendation regarding at least one feature identifiable within the pixel data of the new image; and rendering, on a display screen of a user computing device of the user, the new user-specific recommendation or comment.

17. The digital imaging method of aspect 16, wherein a delta trapped hair value is generated based on a comparison between the new user-specific trapped hair value and the user-specific trapped hair value, wherein the new user-specific recommendation is further based on the delta trapped hair value, and wherein the delta trapped hair value is rendered on the display screen of the user computing device.

18. The digital imaging method of any of aspects 1-17, wherein the at least one image comprises a plurality of images.

19. The digital imaging method of aspect 18, wherein the plurality of images are collected using a digital video camera.

20. The digital imaging method of any of aspects 1-19, wherein the user's hair is removed by a wet razor, a dry shaver, an epilator, or a wax.

21. The digital imaging method of any of aspects 1-20, wherein the trapped hair value is based at least partially on a number of trapped hairs.

22. The digital imaging method of any of aspects 1-21, wherein the trapped hair value is based at least partially on a severity of trapped hairs.

23. The digital imaging method of any of aspects 1-22, wherein the at least one image is captured by a digital camera within a threshold timeframe prior to hair removal.

24. The digital imaging method of aspect 23, wherein the threshold timeframe is a twelve hour timeframe prior to hair removal.

25. A digital imaging system configured to analyze pixel data of at least one image of a user's body for determining a user-specific trapped hair value before removing hair, the digital imaging system comprising: an imaging server comprising a server processor and a server memory; an imaging application (app) configured to execute on a user computing device comprising a device processor and a device memory, the imaging app communicatively coupled to the imaging server; and a trapped hair model trained with pixel data of a plurality of training images of individuals and operable to determine trapped hair values associated with a trapped hair scale ranging from least trapped hair to most trapped hair, wherein the trapped hair model is configured to execute on the server processor or the device processor to cause the server processor or the device processor to: receive at least one image of a user, the at least one image captured by a digital camera, and the at least one image comprising pixel data of the user's body or body area before removing hair, analyze, by the trapped hair model, the at least one image captured by the digital camera to determine a user-specific trapped hair value, generate, based on the user-specific trapped hair value, at least one user-specific electronic recommendation designed to address at least one feature identifiable within the pixel data comprising the user's body or body area before removing hair, and render, on a display screen of the user computing device of the user, the at least one user-specific electronic recommendation.

26. A tangible, non-transitory computer-readable medium storing instructions for analyzing pixel data of at least one image of a user's body for determining a user-specific trapped hair value before removing hair, that when executed by one or more processors cause the one or more processors to: aggregate, at one or more processors communicatively coupled to one or more memories, a plurality of training images of a plurality of individuals, each of the training images comprising pixel data of a respective individual before removing hair; train, by the one or more processors with the pixel data of the plurality of training images, a trapped hair model operable to determine trapped hair values associated with a trapped hair scale ranging from least trapped hair to most trapped hair; receive, at the one or more processors, at least one image of a user, the at least one image captured by a digital camera, and the at least one image comprising pixel data of the user's body or body area before removing hair; analyze, by the trapped hair model executing on the one or more processors, the at least one image captured by the digital camera to determine a user-specific trapped hair value; generate, by the one or more processors based on the user-specific trapped hair value, at least one user-specific electronic recommendation designed to address at least one feature identifiable within the pixel data comprising the user's body or body area before removing hair; and render, on a display screen of a user computing device, the at least one user-specific electronic recommendation.

ADDITIONAL CONSIDERATIONS

Although the disclosure herein sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed before the filing date of this patent, which would still fall within the scope of the claims.

The following additional considerations apply to the foregoing discussion. Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location, while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other embodiments, the one or more processors or processor-implemented modules may be distributed across a number of geographic locations.

This detailed description is to be construed as exemplary only and does not describe every possible embodiment, as describing every possible embodiment would be impractical, if not impossible. A person of ordinary skill in the art may implement numerous alternate embodiments, using either current technology or technology developed before the filing date of this application.

Those of ordinary skill in the art will recognize that a wide variety of modifications, alterations, and combinations can be made with respect to the above described embodiments without departing from the scope of the invention, and that such modifications, alterations, and combinations are to be viewed as being within the ambit of the inventive concept.

The patent claims at the end of this patent application are not intended to be construed under 35 U.S.C. § 112(f) unless traditional means-plus-function language is expressly recited, such as "means for" or "step for" language being explicitly recited in the claim(s). The systems and methods described herein are directed to an improvement to computer functionality, and improve the functioning of conventional computers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited.

The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A digital imaging method of analyzing pixel data of at least one image of a user's body for determining a user-specific trapped hair value before removing hair, the digital imaging method comprising the steps of:
   aggregating, at one or more processors communicatively coupled to one or more memories, a plurality of training images of a plurality of individuals before removing hair, each of the training images comprising pixel data of a respective individual's body or body area before removing hair;
   training, by the one or more processors, with the pixel data of the plurality of training images, a trapped hair model operable to determine trapped hair values associated with a trapped hair scale ranging from least trapped hair to most trapped hair, wherein the trapped hair values are based at least partially on a number of trapped hairs;
   receiving, at the one or more processors, at least one image of a user, the at least one image captured by a digital camera, and the at least one image comprising pixel data of the user's body or body area before removing hair;
   analyzing by the trapped hair model executing on the one or more processors, the at least one image captured by the digital camera to determine a user-specific trapped hair value and a corresponding location identifier indicating a body area location of the user's body or body area, wherein the body area location comprises the user's face, the user's cheek, the user's neck, the user's jaw, the user's head, the user's groin, the user's underarm, the user's chest, the user's back, the user's leg, the user's arm, or the user's bikini area;
   generating, by the one or more processors, based on the user-specific trapped hair value, at least one user-specific electronic recommendation designed to address at least one feature identifiable within the pixel data of the user's body or body area; and
   rendering, on a display screen of a user computing device, the at least one user-specific electronic recommendation.

2. The digital imaging method of claim 1, wherein the at least one user-specific electronic recommendation is displayed on the display screen of the user computing device with a graphical representation of the user's body or body area as annotated with one or more graphics or textual renderings corresponding to the user-specific trapped hair value.

3. The digital imaging method of claim 1, wherein the at least one user-specific electronic recommendation is a recommendation for a manufactured product.

4. The digital imaging method of claim 3, wherein the at least one user-specific electronic recommendation is displayed on the display screen of the user computing device with instructions for treating, with the manufactured product, the at least one feature identifiable within the pixel data of the user's body or body area.

5. The digital imaging method of claim 4, further comprising the steps of: initiating, by the one or more processors, based on the recommendation for the manufactured product, the manufactured product for shipment to the user.

6. The digital imaging method of claim 1, wherein the at least one user-specific electronic recommendation is rendered or transmitted for rendering in real-time or near-real time.

7. The digital imaging method of claim 6, further comprising:
   generating, by the one or more processors, a modified image based on the at least one image, the modified image depicting how the user's body or body area is predicted to appear after treating the at least one feature with the manufactured product; and
   rendering, on the display screen of the user computing device, the modified image.

8. The digital imaging method of claim 1, wherein the trapped hair model is an artificial intelligence (AI) based model trained with at least one AI algorithm.

9. The digital imaging method of claim 1, wherein the one or more processors comprises at least one of a server or a cloud-based computing platform, and the server or the cloud-based computing platform receives the plurality of training images of the plurality of individuals via a computer network, and wherein the server or the cloud-based computing platform trains the trapped hair model with the pixel data of the plurality of training images.

10. The digital imaging method of claim 9, wherein the server or a cloud-based computing platform receives the at least one image comprising the pixel data of the user's body before removing hair, and wherein the server or a cloud-based computing platform executes the trapped hair model and generates, based on output of the trapped hair model, the user-specific recommendation and transmits, via the computer network, the user-specific recommendation to the user computing device for rendering on the display screen of the user computing device.

11. The digital imaging method of claim 1, wherein the user computing device comprises a mobile device, a tablet, a handheld device, a desktop device, a personal assistant device, a home assistant device, or a retail device.

12. The digital imaging method of claim 1, wherein the user computing device receives the at least one image comprising the pixel data of the at least a portion of the user's body before removing hair, and wherein the user computing device executes the trapped hair model and generates, based on output of the trapped hair model, the user-specific recommendation, and renders the user-specific recommendation on the display screen of the user computing device.

13. The digital imaging method of claim 1, wherein the user-specific recommendation includes a recommended of a behavior selected, by the one or more processors, from at least two available behaviors based upon the trapped hair value.

14. The digital method of claim 1, further comprising:
   receiving, at the one or more processors, a new image of the user, the new image captured by the digital camera, and the new image comprising pixel data of the user's body at a body area location before removing hair;

analyzing, by the trapped hair model executing on the one or more processors, the new image captured by the digital camera to determine a new user-specific trapped hair value;

generating, based on the new user-specific trapped hair value, a new user-specific electronic recommendation regarding at least one feature identifiable within the pixel data of the new image; and rendering, on a display screen of a user computing device of the user, the new user-specific recommendation or comment.

15. The digital imaging method of claim 14, wherein a delta trapped hair value is generated based on a comparison between the new user-specific trapped hair value and the user-specific trapped hair value, wherein the new user-specific recommendation is further based on the delta trapped hair value, and wherein the delta trapped hair value is rendered on the display screen of the user computing device.

16. The digital imaging method of claim 1, wherein the at least one image comprises a plurality of images.

17. The digital imaging method of claim 16, wherein the plurality of images are collected using a digital video camera.

18. The digital imaging method of claim 1, wherein the user's hair is removed by a wet razor, a dry shaver, an epilator, or a wax.

19. The digital imaging method of claim 1, wherein the trapped hair value is based at least partially on a severity of trapped hairs.

20. The digital imaging method of claim 1, wherein the at least one image is captured by a digital camera within a threshold timeframe before hair removal.

21. The digital imaging method of claim 20, wherein the threshold timeframe is a twelve hour timeframe.

22. A digital imaging system configured to analyze pixel data of at least one image of a user's body for determining a user-specific trapped hair value before removing hair, the digital imaging system comprising:

an imaging server comprising a server processor and a server memory;

an imaging application (app) configured to execute on a user computing device comprising a device processor and a device memory, the imaging app communicatively coupled to the imaging server; and a trapped hair model trained with pixel data of a plurality of training images of individuals and operable to determine trapped hair values associated with a trapped hair scale ranging from least trapped hair to most trapped hair, wherein the trapped hair values are based at least partially on a number of trapped hairs, wherein the trapped hair model is configured to execute on the server processor or the device processor to cause the server processor or the device processor to:

receive at least one image of a user, the at least one image captured by a digital camera, and the at least one image comprising pixel data of the user's body or body area before removing hair, analyze, by the trapped hair model, the at least one image captured by the digital camera to determine a user-specific trapped hair value and a corresponding location identifier indicating a body area location of the user's body or body area, wherein the body area location comprises the user's face, the user's cheek, the user's neck, the user's jaw, the user's head, the user's groin, the user's underarm, the user's chest, the user's back, the user's leg, the user's arm, or the user's bikini area, generate, based on the user-specific trapped hair value, at least one user-specific electronic recommendation designed to address at least one feature identifiable within the pixel data comprising the user's body or body area before removing hair, and render, on a display screen of the user computing device of the user, the at least one user-specific electronic recommendation.

23. A tangible, non-transitory computer-readable medium storing instructions for analyzing pixel data of at least one image of a user's body for determining a user-specific trapped hair value before removing hair, that when executed by one or more processors cause the one or more processors to:

aggregate, at one or more processors communicatively coupled to one or more memories, a plurality of training images of a plurality of individuals, each of the training images comprising pixel data of a respective individual before removing hair;

train, by the one or more processors with the pixel data of the plurality of training images, a trapped hair model operable to determine trapped hair values associated with a trapped hair scale ranging from least trapped hair to most trapped hair, wherein the trapped hair values are based at least partially on a number of trapped hairs;

receive, at the one or more processors, at least one image of a user, the at least one image captured by a digital camera, and the at least one image comprising pixel data of the user's body or body area before removing hair;

analyze, by the trapped hair model executing on the one or more processors, the at least one image captured by the digital camera to determine a user-specific trapped hair value and a corresponding location identifier indicating a body area location of the user's body or body area, wherein the body area location comprises the user's face, the user's cheek, the user's neck, the user's jaw, the user's head, the user's groin, the user's underarm, the user's chest, the user's back, the user's leg, the user's arm, or the user's bikini area;

generate, by the one or more processors based on the user-specific trapped hair value, at least one user-specific electronic recommendation designed to address at least one feature identifiable within the pixel data comprising the user's body or body area before removing hair; and render, on a display screen of a user computing device, the at least one user-specific electronic recommendation.

\* \* \* \* \*